United States Patent [19]

Cortes

[11] Patent Number: 5,414,136
[45] Date of Patent: May 9, 1995

[54] METHOD FOR THE PREPARATION OF 4-HALO-2'-NITROBUTYROPHENONE COMPOUNDS

[75] Inventor: David A. Cortes, Fairless Hills, Pa.

[73] Assignee: American Cyanamid, Wayne, N.J.

[21] Appl. No.: 235,579

[22] Filed: Apr. 29, 1994

[51] Int. Cl.⁶ .............................................. C07C 45/65
[52] U.S. Cl. ...................................................... 568/306
[58] Field of Search ................................. 568/306, 319

[56] References Cited

U.S. PATENT DOCUMENTS

| | | | |
|---|---|---|---|
| 4,075,346 | 2/1978 | Sasajima et al. | 568/306 |
| 4,622,065 | 11/1986 | Van Gemert | 71/93 |
| 5,009,699 | 4/1991 | Brady et al. | 71/92 |
| 5,280,007 | 1/1994 | Kawai | 504/105 |

OTHER PUBLICATIONS

Y. Kuwayama, Chemicals Pharm. Bulletin, 9, pp. 719–721 (1961).

*Primary Examiner*—James H. Reamer
*Attorney, Agent, or Firm*—Peggy Ann Climenson

[57] ABSTRACT

The present invention provides a method for the preparation of a 4-halo-2'-nitrobutyrophenone compound having the structural formula I

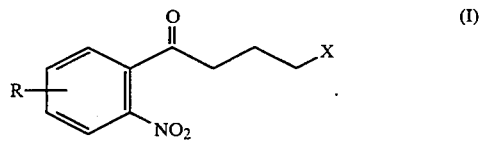

The formula I compound is an important intermediate in the manufacture of a sulfamoyl urea herbicidal agent.

10 Claims, No Drawings

METHOD FOR THE PREPARATION OF 4-HALO-2'-NITROBUTYROPHENONE COMPOUNDS

BACKGROUND OF THE INVENTION

Herbicidal sulfamoyl urea compounds are described in U.S. Pat. Nos. 4,622,065, 5,009,699 and 5,280,007, among others. The crop-selective sulfamoyl urea herbicidal agent 1-{[o-(cyclopropylcarbonyl)-phenyl]sulfamoyl}-3-(4,6-dimethoxy-2-pyrimidinyl)urea is described in U.S. Pat. No. 5,009,699. This sulfamoyl urea compound demonstrates a superior margin of safety toward crop plants, especially rice plants, while concomitantly controlling broadleaf weeds and sedges.

4-Halo-2'-nitrobutyrophenone compounds are key intermediates in the preparation of sulfamoyl urea herbicides. 4-Halo-2'-nitrobutyrophenone compounds and their multi-step preparations from the magnesium enolate of acetylbutyrolactone are described in U.S. Pat. No. 4,075,346 and copending U.S. patent application Ser. No. 08/161,382 filed on Dec. 2, 1993. However, these methods require multiple chemical reactions which increase chemical waste and reduce cost-effectiveness.

It is an object of the present invention to provide an efficient single-step method for the preparation of 4-halo-2'-nitrobutyrophenone compounds which eliminates the use of hydrogen halide reactants, reduces waste and increases cost-efficiency.

SUMMARY OF THE INVENTION

The present invention relates to a single-step method for the preparation of 4-halo-2'-nitrobutyrophenone compounds from 2-nitrobenzoyl halide compounds and the magnesium enolate of acetylbutyrolactone.

The 4-halo-2'-nitrobutyrophenone compounds are important intermediates in the manufacture of sulfamoyl urea compounds.

DETAILED DESCRIPTION OF THE INVENTION

The present invention relates to a method for the preparation of a 4-halo-2'-nitrobutyrophenone compound having the structural formula I

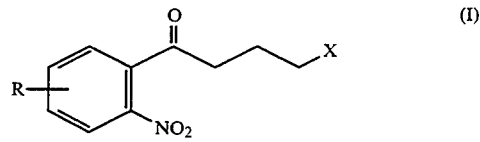

wherein
X is Cl or Br; and
R is hydrogen, halogen, $C_1$-$C_4$alkyl or $C_1$-$C_4$haloalkyl, which comprises reacting a 2-nitrobenzoyl halide compound having the structural formula II

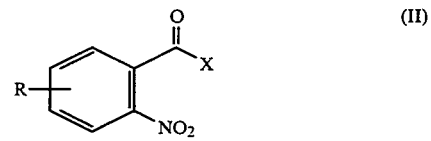

wherein X and R are as described above with at least one molar equivalent of the magnesium enolate of acetylbutyrolactone in the presence of a solvent at an elevated temperature and optionally concentrating the resultant reaction mixture by distillation of the solvent to form the desired formula I compound.

Exemplary of halogen hereinabove are fluorine, chlorine, bromine and iodine. The term "$C_1$-$C_4$haloalkyl" is defined as a $C_1$-$C_4$alkyl group substituted with one or more halogen atoms.

Uniquely, it has been found that 4-halo-2'-nitrobutyrophenone compounds are prepared directly from the reaction of a 2-nitrobenzoyl halide compound and the magnesium enolate of acetylbutyrolactone. The reaction scheme is shown in Flow Diagram I.

FLOW DIAGRAM I

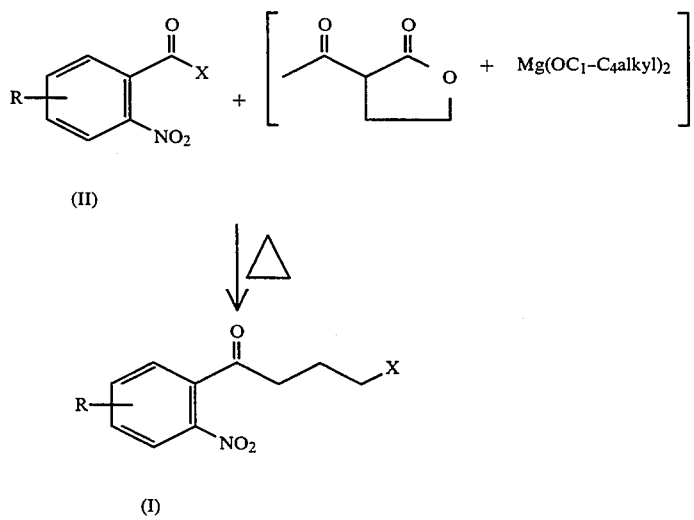

Advantageously, the method of the present invention avoids multi-step procedures such as deacylation and hydrohalogenation. Further, the inventive method reduces waste and eliminates the use of hydrogen halides.

The 4-halo-2'-nitrobutyrophenone compounds may then be readily converted to 2-aminophenyl cyclopropyl ketone compounds as shown in Flow Diagram II.

FLOW DIAGRAM II

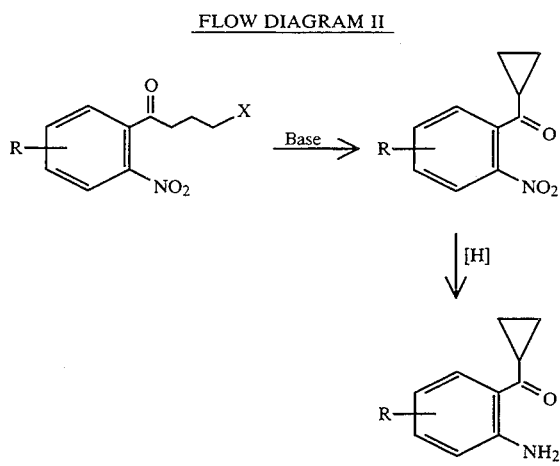

2-Aminophenyl cyclopropyl ketone compounds may then be converted to sulfamoyl urea compounds as shown in Flow Diagram III.

FLOW DIAGRAM III

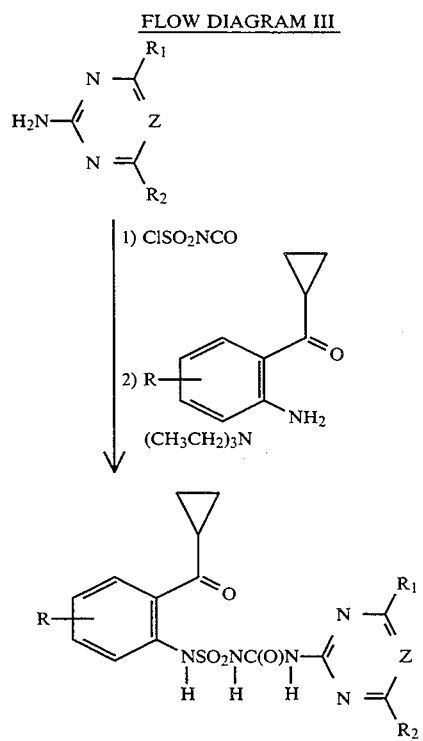

wherein
R is hydrogen, halogen, $C_1$–$C_4$alkyl or $C_1$–$C_4$haloalkyl;
Z is N or CH; and
$R_1$ and $R_2$ are each independently halogen, $C_1$–$C_6$alkyl or $C_1$–$C_6$alkoxy.

Preferred 4-halo-2'-nitrobutyrophenone compounds prepared by the method of the present invention are those wherein
X is Cl or Br; and
R is hydrogen or halogen.

More preferred formula I compounds prepared by the method of this invention are those wherein
X is Cl or Br; and
R is hydrogen or 5'-fluoro.

The method of the present invention is especially useful for the preparation of 4-chloro-2'-nitrobutyrophenone, and 4-chloro-5'-fluoro-2'-nitrobutyrophenone.

Solvents suitable for use in the present invention include aromatic hydrocarbons and chlorinated aromatic hydrocarbons such as toluene, o-xylene, m-xylene, p-xylene, benzene, chlorobenzene and the like with toluene being preferred.

The method of the present invention is carried out at an elevated temperature, preferably from about 75° C. to 155° C., more preferably from about 100° C. to 130° C.

The starting magnesium enolate of acetylbutyrolactone and methods for its preparation are described in U.S. Pat. No. 4,075,346 and Chem. Pharm. Bull., 9, pp. 719–721 (1961).

In order to facilitate a further understanding of the invention, the following examples are presented. The invention should not be deemed limited by the examples as the full scope of the invention is defined in the claims.

EXAMPLE 1

Preparation of 4-Chloro-2'-nitrobutyrophenone

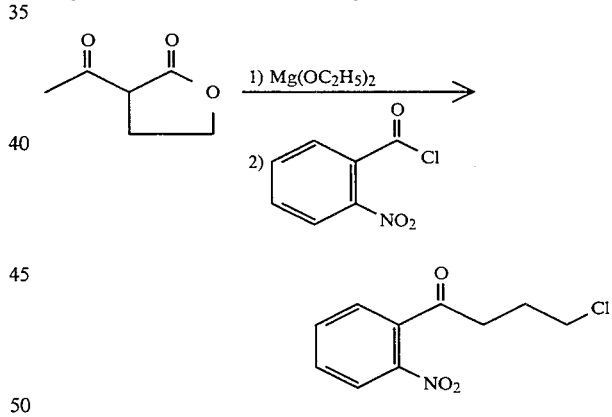

o-Nitrobenzoyl chloride (0.050 mol as a 20% solution in toluene) is added to the magnesium enolate of acetylbutyrolactone, prepared from a mixture of magnesium ethoxide (3.1 g, 0.027 mol) and acetylbutyrolactone (7.1 g, 0.055 mol) in toluene (25 mL). The reaction mixture is heated to and held at 110° to 123° C. for about two hours during which time most of the toluene is allowed to distill. The reaction mixture is then cooled and diluted with an ethyl acetate/water mixture. The organic phase is separated and concentrated in vacuo to give the title product as an oil (9.0 g, 45% real, 35% yield).

EXAMPLE 2

Preparation of 4-Chloro-5'-fluoro-2'-nitrobutyrophenone

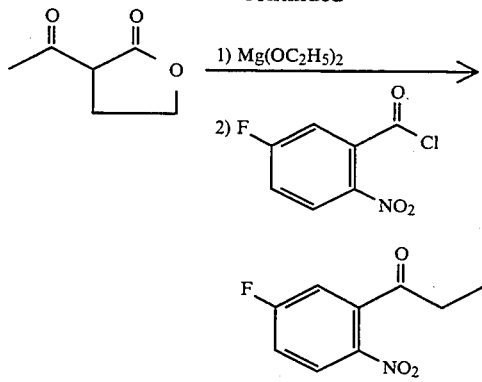

5-Fluoro-2-nitrobenzoyl chloride (37.5 mmol as a solution in toluene) is added to the magnesium enolate of acetylbutyrolactone, prepared from a mixture of magnesium ethoxide (2.32 g, 20.3 mmol) and acetylbutyrolactone (5.33 g, 41.3 mmol) in toluene. The reaction mixture is heated to and held at 110° to 125° C. for about 2.5 hours during which time most of the toluene is allowed to distill. The reaction mixture is then cooled and diluted with an ethyl acetate/water mixture. The organic phase is separated and concentrated in vacuo to give the title product as an oil.

EXAMPLE 3

Preparation of o-nitrophenyl cyclopropyl ketone

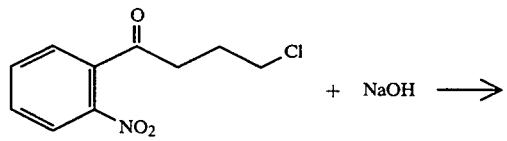

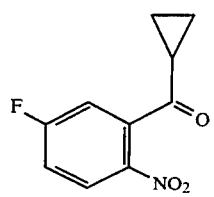

A stirred mixture of 4-chloro-2'-nitrobutyrophenone (2.96 g, 0.013 mol) and sodium hydroxide (0.76 g, 0.019 mol) in water is heated at reflux until the reaction is complete by thin layer chromatography analysis, cooled to room temperature and extracted with diethyl ether. The organic extracts are combined, dried over anhydrous sodium sulfate and concentrated in vacuo to give a residue. The residue is taken up in diethyl ether, filtered through silica gel and concentrated in vacuo to give the title product as a yellow oil.

EXAMPLE 4

Preparation of 5-Fluoro-2-nitrophenyl cyclopropyl ketone

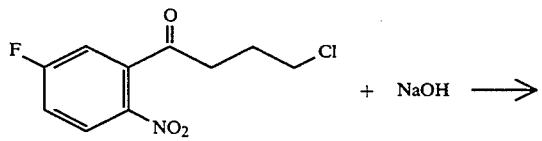

A stirred mixture of 4-chloro-5'-fluoro-2'-nitrobutyrophenone (2.65 g, 10.8 mmol) and sodium hydroxide (0.63 g, 15.8 mmol) in water is heated at reflux, cooled and extracted with diethyl ether. The organic extracts are combined, dried over anhydrous sodium sulfate and concentrated in vacuo to give the title product as an oil.

EXAMPLE 5

Preparation of o-amiophenyl cyclopropyl ketone

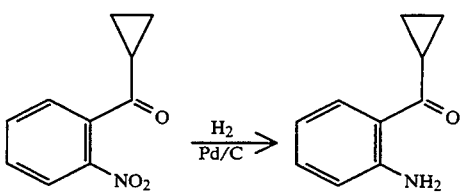

A mixture of o-nitrophenyl cyclopropyl-ketone (100 mg, 0.52 mmol) and a catalytic amount of 10% palladium on carbon in methanol is stirred under hydrogen at atmospheric pressure until reaction is complete by thin layer chromatography analysis. The reaction mixture is filtered and the filtrate is concentrated in vacuo to give a bright yellow oil. The oil is flash cromatographed to give the title product as an off-white crystalline solid.

EXAMPLE 6

Preparation of 2-Amino-5-fluorophenyl cyclopropyl ketone

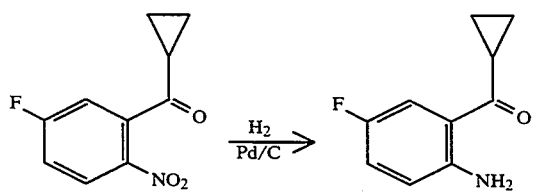

A mixture of 5-fluoro-2-nitrophenyl cyclopropyl ketone (98 mg, 0.47 mmol) and a catalytic amount of 10% palladium on carbon in methanol is stirred under hydrogen at atmospheric pressure. The reaction mixture is then filtered and the filtrate is concentrated in vacuo to give the title product as an oil.

I claim:

1. A method for the preparation of a 4-halo-2'-nitrobutyrophenone compound having the structural formula

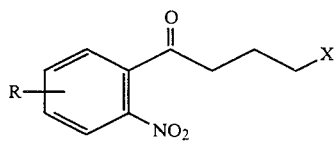

wherein
X is Cl or Br; and
R is hydrogen, halogen, $C_1$-$C_4$alkyl or $C_1$-$C_4$haloalkyl, which comprises reacting a 2-nitrobenzoyl halide compound having the structural formula

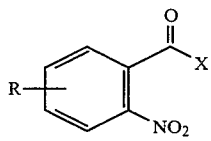

wherein X and R are as described above with at least one molar equivalent of the magnesium enolate of acetylbutyrolactone in the presence of a solvent at an elevated temperature and optionally concentrating the resultant reaction mixture by distillation of the solvent.

2. The method according to claim 1 wherein the elevated temperature is about 75° C. to 155° C.

3. The method according to claim 2 wherein the temperature is about 100° C. to 130° C.

4. The method according to claim 1 wherein the solvent is selected from the group consisting of an aromatic hydrocarbon and a chlorinated aromatic hydrocarbon.

5. The method according to claim 4 wherein the solvent is selected from the group consisting of toluene, o-xylene, m-xylene, p-xylene, benzene and chlorobenzene.

6. The method according to claim 5 wherein the solvent is toluene.

7. The method according to claim 1 wherein
X is Cl or Br; and
R is hydrogen or halogen.

8. The method according to claim 7 wherein
X is Cl or Br; and
R is hydrogen or 5'-fluoro.

9. The method according to claim 8 wherein
X is Cl; and
R is hydrogen.

10. The method according to claim 1 wherein the resultant reaction mixture is concentrated by distillation of the solvent.

* * * * *